United States Patent
Ortiz et al.

(10) Patent No.: US 7,896,890 B2
(45) Date of Patent: Mar. 1, 2011

(54) METHOD AND APPARATUS FOR ENDOSCOPICALLY PERFORMING GASTRIC REDUCTION SURGERY IN A SINGLE STEP

(75) Inventors: Mark S. Ortiz, Milford, OH (US);
Michael J. Stokes, Cincinnati, OH (US);
William J. Kraimer, Mason, OH (US);
David B. Griffith, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 829 days.

(21) Appl. No.: 11/217,672

(22) Filed: Sep. 2, 2005

(65) Prior Publication Data

US 2007/0055292 A1 Mar. 8, 2007

(51) Int. Cl.
*A61B 17/10* (2006.01)

(52) U.S. Cl. ......... 606/139; 606/142; 606/143; 606/151; 606/219; 227/175.1; 227/176.1

(58) Field of Classification Search .................. 606/149, 606/151, 213, 139, 142, 143, 144, 153, 215, 606/216, 219, 221; 227/19, 175.1, 176.1, 227/179.1, 181.1; 24/709.5
See application file for complete search history.

(56) References Cited

U.S. PATENT DOCUMENTS

| | | | | |
|---|---|---|---|---|
| 4,531,522 A | * | 7/1985 | Bedi et al. ...................... | 606/220 |
| 4,981,149 A | * | 1/1991 | Yoon et al. .................... | 128/898 |
| 5,080,663 A | | 1/1992 | Mills et al. | |
| 5,368,599 A | * | 11/1994 | Hirsch et al. .................. | 606/139 |
| 5,376,101 A | | 12/1994 | Green et al. | |
| 5,382,231 A | * | 1/1995 | Shlain ............................ | 128/898 |
| 5,423,857 A | * | 6/1995 | Rosenman et al. ............ | 606/219 |
| 5,437,681 A | | 8/1995 | Meade et al. | |
| 5,462,558 A | | 10/1995 | Kolesa et al. | |
| 5,514,159 A | | 5/1996 | Matula et al. | |
| 5,540,705 A | | 7/1996 | Meade et al. | |
| 5,571,119 A | | 11/1996 | Atala | |
| 5,573,543 A | | 11/1996 | Akopov et al. | |
| 5,709,693 A | | 1/1998 | Taylor | |
| 5,713,910 A | | 2/1998 | Gordon et al. | |
| 5,792,153 A | * | 8/1998 | Swain et al. ................... | 606/144 |
| 5,814,071 A | | 9/1998 | McDevitt et al. | |
| 5,947,983 A | * | 9/1999 | Solar et al. .................... | 606/144 |
| 5,976,161 A | * | 11/1999 | Kirsch et al. .................. | 606/149 |
| 6,036,694 A | | 3/2000 | Goble et al. | |
| 6,159,146 A | * | 12/2000 | El Gazayerli ................. | 600/106 |
| 6,313,993 B1 | * | 11/2001 | Hinshaw et al. .............. | 361/704 |

(Continued)

FOREIGN PATENT DOCUMENTS

EP 1545336 6/2005

(Continued)

*Primary Examiner* — Todd E Manahan
*Assistant Examiner* — Erin Colello
(74) *Attorney, Agent, or Firm* — Welsh Flaxman & Gitler LLC

(57) ABSTRACT

An endoscopic gastric reduction apparatus adapted for applying a series of pledgets to anterior and posterior gastric walls for the creation of a mattress stitch suture within the stomach includes an applier having a distal end and a proximal end. The applier is secured at a distal end of a support shaft shaped and dimensioned for passage down the esophagus and into the stomach. The applier includes an applier body having a suction slot shaped and dimensioned for receiving tissue therein for the application of at least one pledget housed within the suction slot for selective coupling with tissue suctioned within the suction slot.

30 Claims, 8 Drawing Sheets

U.S. PATENT DOCUMENTS

| | | | |
|---|---|---|---|
| 6,346,111 B1 | 2/2002 | Gordon et al. | |
| 6,358,197 B1 * | 3/2002 | Silverman et al. | 600/29 |
| 6,443,962 B1 | 9/2002 | Gaber | |
| 6,454,778 B2 | 9/2002 | Kortenbach | |
| 6,494,888 B1 * | 12/2002 | Laufer et al. | 606/153 |
| 6,506,196 B1 | 1/2003 | Laufer | |
| 6,558,400 B2 * | 5/2003 | Deem et al. | 606/151 |
| 6,592,596 B1 * | 7/2003 | Geitz | 606/139 |
| 6,656,194 B1 | 12/2003 | Gannoe et al. | |
| 6,663,639 B1 | 12/2003 | Laufer et al. | |
| 6,716,222 B2 * | 4/2004 | McAlister et al. | 606/139 |
| 6,719,763 B2 | 4/2004 | Chung et al. | |
| 6,719,764 B1 | 4/2004 | Gellman et al. | |
| 6,746,460 B2 | 6/2004 | Gannoe et al. | |
| 6,755,843 B2 | 6/2004 | Chung et al. | |
| 6,773,440 B2 * | 8/2004 | Gannoe et al. | 606/142 |
| 6,835,200 B2 * | 12/2004 | Laufer et al. | 606/153 |
| 6,908,427 B2 | 6/2005 | Fleener et al. | |
| 6,923,819 B2 | 8/2005 | Meade et al. | |
| 7,001,412 B2 * | 2/2006 | Gallagher et al. | 606/232 |
| 7,083,629 B2 * | 8/2006 | Weller et al. | 606/151 |
| 7,097,650 B2 * | 8/2006 | Weller et al. | 606/153 |
| 7,235,089 B1 * | 6/2007 | McGuckin, Jr. | 606/167 |
| 7,261,722 B2 * | 8/2007 | McGuckin et al. | 606/139 |
| 7,306,614 B2 * | 12/2007 | Weller et al. | 606/151 |
| 7,334,718 B2 * | 2/2008 | McAlister et al. | 227/175.1 |
| 2001/0023352 A1 | 9/2001 | Gordon et al. | |
| 2002/0082621 A1 * | 6/2002 | Schurr et al. | 606/151 |
| 2002/0107530 A1 | 8/2002 | Sauer et al. | |
| 2002/0107531 A1 * | 8/2002 | Schreck et al. | 606/142 |
| 2003/0065359 A1 * | 4/2003 | Weller et al. | 606/213 |
| 2003/0083674 A1 | 5/2003 | Gibbens, III | |
| 2003/0171760 A1 * | 9/2003 | Gambale | 606/139 |
| 2003/0181924 A1 | 9/2003 | Yamamoto et al. | |
| 2003/0208209 A1 * | 11/2003 | Gambale et al. | 606/144 |
| 2003/0233104 A1 | 12/2003 | Gellman et al. | |
| 2003/0233108 A1 | 12/2003 | Gellman et al. | |
| 2004/0006351 A1 * | 1/2004 | Gannoe et al. | 606/139 |
| 2004/0034369 A1 | 2/2004 | Sauer et al. | |
| 2004/0044354 A1 | 3/2004 | Gannoe et al. | |
| 2004/0049209 A1 * | 3/2004 | Benchetrit | 606/151 |
| 2004/0059350 A1 | 3/2004 | Gordon et al. | |
| 2004/0059357 A1 * | 3/2004 | Koseki | 606/151 |
| 2004/0082963 A1 | 4/2004 | Gannoe et al. | |
| 2004/0088008 A1 | 5/2004 | Gannoe et al. | |
| 2004/0122452 A1 * | 6/2004 | Deem et al. | 606/151 |
| 2004/0122473 A1 | 6/2004 | Ewers et al. | |
| 2004/0138682 A1 | 7/2004 | Onuki et al. | |
| 2004/0147941 A1 | 7/2004 | Takemoto et al. | |
| 2004/0147958 A1 | 7/2004 | Lam et al. | |
| 2004/0158125 A1 * | 8/2004 | Aznoian et al. | 600/106 |
| 2004/0162568 A1 | 8/2004 | Saadat et al. | |
| 2004/0172047 A1 | 9/2004 | Gellman et al. | |
| 2004/0186515 A1 * | 9/2004 | Rosenblatt | 606/228 |
| 2004/0193190 A1 | 9/2004 | Liddicoat et al. | 606/153 |
| 2004/0194790 A1 * | 10/2004 | Laufer et al. | 128/898 |
| 2004/0210243 A1 | 10/2004 | Gannoe et al. | |
| 2004/0260344 A1 | 12/2004 | Lyons et al. | |
| 2005/0015101 A1 | 1/2005 | Gibbens, III et al. | |
| 2005/0055038 A1 * | 3/2005 | Kelleher et al. | 606/151 |
| 2005/0070931 A1 | 3/2005 | Li et al. | |
| 2005/0075653 A1 * | 4/2005 | Saadat et al. | 606/139 |
| 2005/0075654 A1 | 4/2005 | Kelleher | |
| 2005/0080438 A1 * | 4/2005 | Weller et al. | 606/153 |
| 2005/0192599 A1 * | 9/2005 | Demarais | 606/151 |
| 2005/0203547 A1 * | 9/2005 | Weller et al. | 606/139 |
| 2005/0261711 A1 * | 11/2005 | Okada et al. | 606/153 |
| 2006/0253126 A1 * | 11/2006 | Bjerken et al. | 606/139 |
| 2009/0125040 A1 * | 5/2009 | Hambly et al. | 606/148 |

FOREIGN PATENT DOCUMENTS

| | | |
|---|---|---|
| EP | 1569709 | 9/2005 |
| EP | 1584294 | 10/2005 |
| WO | WO0061012 | 10/2000 |
| WO | WO 01/10312 | 2/2001 |
| WO | WO0166001 | 9/2001 |
| WO | WO0189393 | 11/2001 |
| WO | WO 02/35980 | 5/2002 |
| WO | WO 03/053253 | 7/2003 |
| WO | WO 03053253 A1 * | 7/2003 |

* cited by examiner

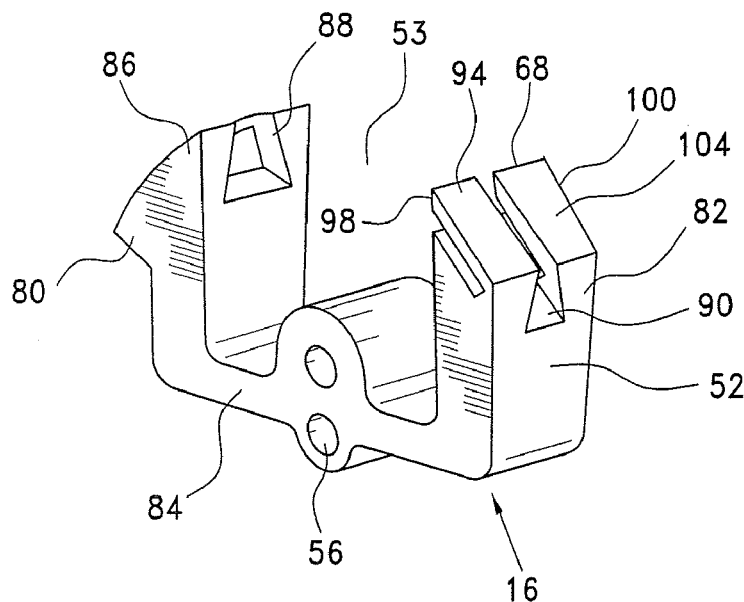
FIG. 4
FIG. 5
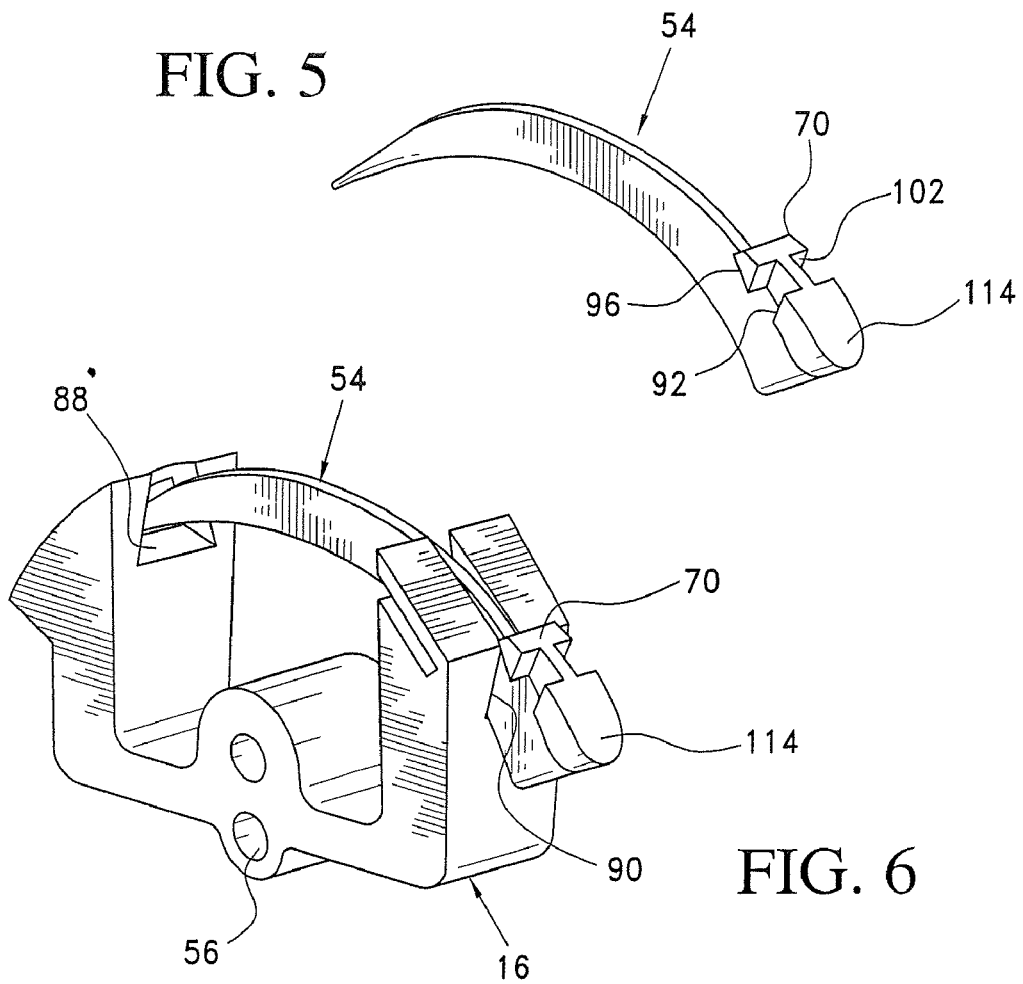
FIG. 6

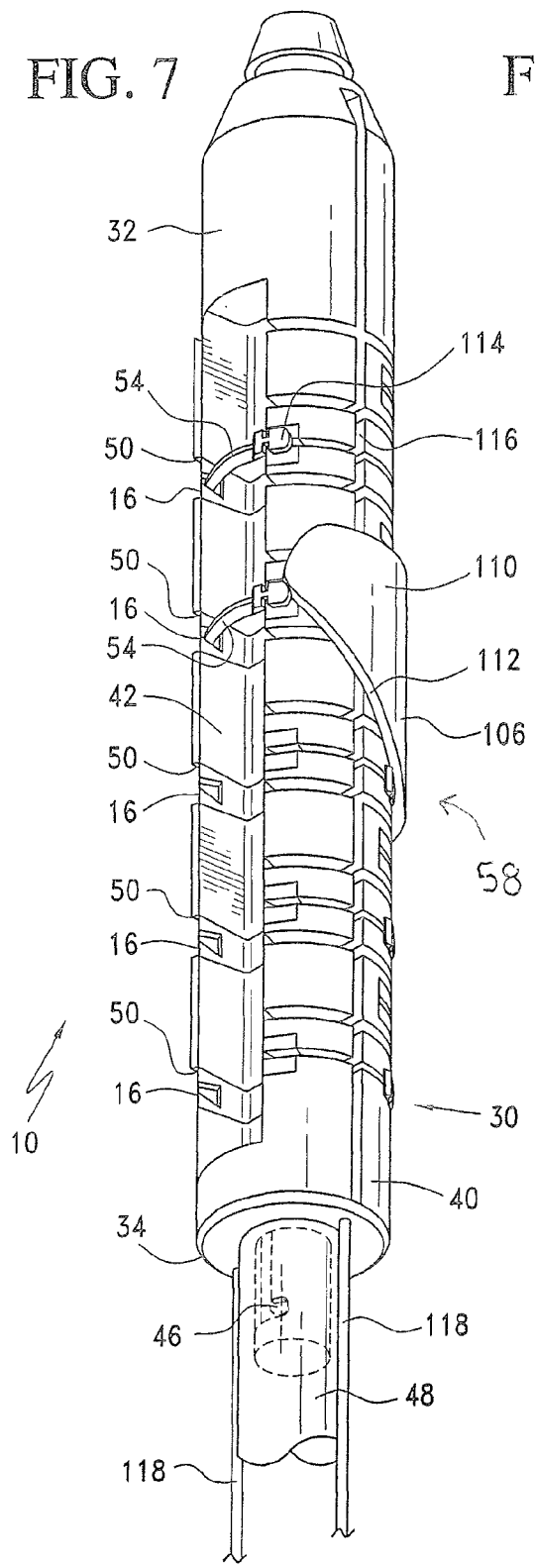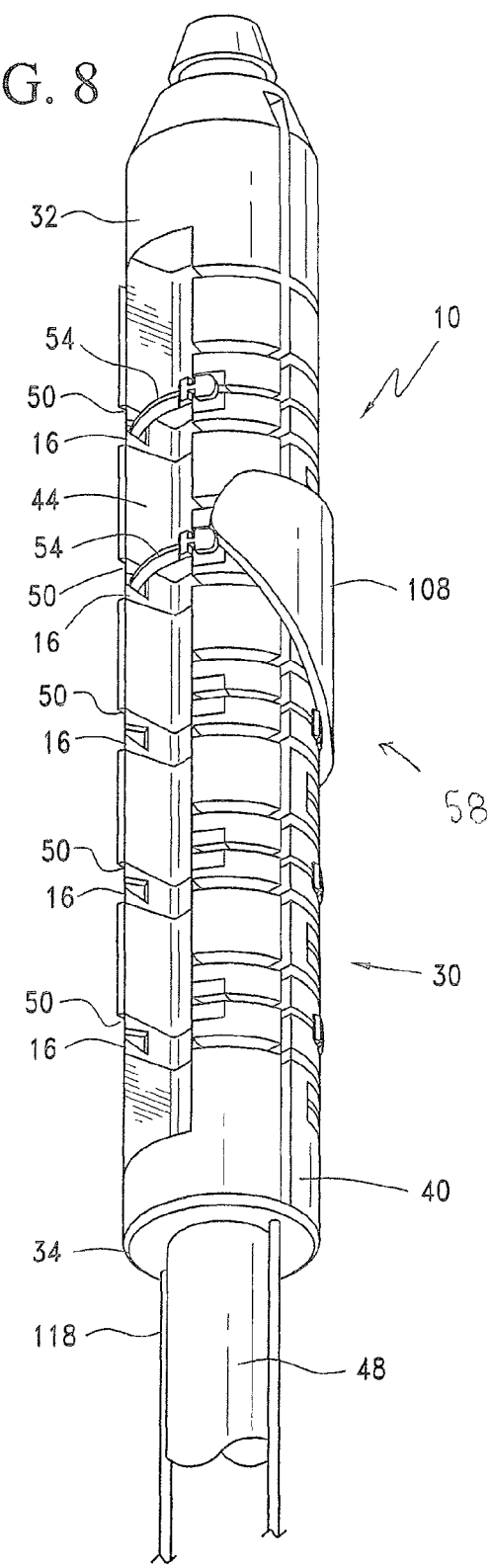

//METHOD AND APPARATUS FOR ENDOSCOPICALLY PERFORMING GASTRIC REDUCTION SURGERY IN A SINGLE STEP

BACKGROUND OF THE INVENTION

1. Field of the Invention

The present invention relates to gastric reduction surgery. More particularly, the inventions to a method and apparatus for endoscopically performing gastric reduction surgery in a single step.

2. Description of the Prior Art

Morbid obesity is a serious medical condition. In fact, morbid obesity has become highly pervasive in the United States, as well as other countries, and the trend appears to be heading in a negative direction. Complications associated with morbid obesity include hypertension, diabetes, coronary artery disease, stroke, congestive heart failure, multiple orthopedic problems and pulmonary insufficiency with markedly decreased life expectancy. With this in mind, and as those skilled in the art will certainly appreciate, the monetary and physical costs associated with morbid obesity are substantial. In fact, it is estimated the costs relating to obesity are in excess of 100 billion dollars in the United States alone.

A variety of surgical procedures have been developed to treat obesity. The most common currently performed procedure is Roux-en-Y gastric bypass (RYGB). This procedure is highly complex and is commonly utilized to treat people exhibiting morbid obesity. However, and with this in mind, greater than 100,000 procedures are performed annually in the United States alone. Other forms of bariatric surgery include Fobi pouch, bilio-pancreatic diversion, and gastroplastic or "stomach stapling". In addition, implantable devices are known which limit the passage of food through the stomach and affect satiety.

RYGB involves movement of the jejunum to a high position using a Roux-en-Y loop. The stomach is completely divided into two unequal portions (a smaller upper portion and a larger lower gastric pouch) using an automatic stapling device. The upper pouch typically measures less than about 1 ounce (or 20 cc), while the larger lower pouch remains generally intact and continues to secrete stomach juices flowing through the intestinal track.

A segment of the small intestine is then brought from the lower abdomen and joined with the upper pouch to form an anastomosis created through a half-inch opening, also called the stoma. This segment of the small intestine is called the "Roux loop" and carries the food from the upper pouch to the remainder of the intestines, where the food is digested. The remaining lower pouch, and the attached segment of duodenum, are then reconnected to form another anastomotic connection to the Roux loop at a location approximately 50 to 150 cm from the stoma, typically using a stapling instrument. It is at this connection that the digestive juices from the bypass stomach, pancreas, and liver, enter the jejunum and ileum to aid in the digestion of food. Due to the small size of the upper pouch, patients are forced to eat at a slower rate and are satiated much more quickly. This results in a reduction in caloric intake.

The conventional RYGB procedure requires a great deal of operative time. Because of the degree of invasiveness, postoperative recovery time can be quite lengthy and painful.

In view of the highly invasive nature of the current RYGB procedure, other less invasive procedures have been developed. The most common form of gastric reduction surgery involves the application of vertical staples along the stomach to create an appropriate pouch. This procedure is commonly performed laparoscopically and, as such, requires substantial preoperative, operative, postoperative resources.

With the foregoing in mind, procedures that allow for the performance of gastric reduction surgery in a time efficient and patient friendly manner are needed. The present invention provides such a method and an associated apparatus.

SUMMARY OF THE INVENTION

It is, therefore, an object of the present invention to provide an endoscopic gastric reduction apparatus adapted for applying a series of pledgets to anterior and posterior gastric walls for the creation of a patterned suture stitch within the stomach. The apparatus includes an applier having a distal end and a proximal end. The applier is secured at a distal end of a support shaft shaped and dimensioned for passage down the esophagus and into the stomach. The applier includes an applier body having a suction slot shaped and dimensioned for receiving tissue therein for application of at least one pledget housed within the suction slot for selective coupling with tissue suctioned within the suction slot.

It is also an object of the present invention to provide a pledget for fastening to tissue. The pledget includes a pledget body supporting a needle for movement relative thereto. The pledget body defines a pledget opening over which the needle moves to close the pledget opening and secure tissue therein. Opposite the pledget opening is a pledget aperture shaped and dimensioned for the passage of a suture prior to use of the pledget.

Other objects and advantages of the present invention will become apparent from the following detailed description when viewed in conjunction with the accompanying drawings, which set forth certain embodiments of the invention.

BRIEF DESCRIPTION OF THE DRAWINGS

FIGS. 4, 5 and 6 are various perspective views of a pledget, and its component parts, in accordance with the present invention.

FIGS. 7 and 8 are perspective views of the anterior and posterior sides of the present apparatus.

DESCRIPTION OF THE PREFERRED EMBODIMENTS

Figure 1:
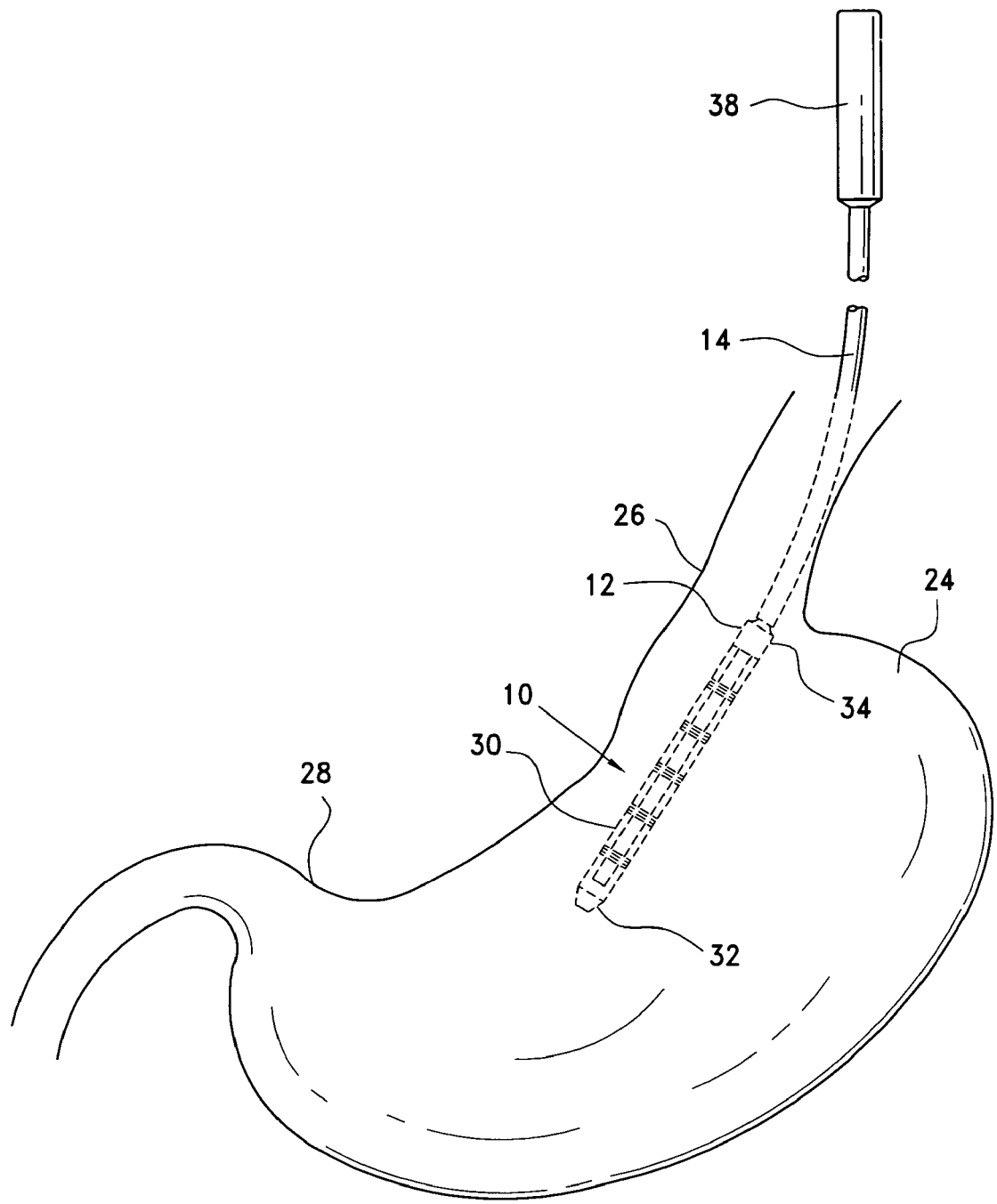
FIG. 1 is a view of the present apparatus positioned within the stomach of an individual.

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as the basis for the claims and as a basis for teaching one skilled in the art how to make and/or use the invention.

Referring to the various FIGS. 1 to 11, an endoscopic gastric reduction apparatus 10 for performing a substantially one-step gastric reduction procedure is disclosed. The gastric reduction apparatus 10 includes an applier 30 secured at the distal end 12 of a support shaft 14 shaped and dimensioned for passage down the esophagus and into the stomach. The gastric reduction apparatus 10 functions to apply a series of fasteners 16, which will be referred to as pledgets, to the anterior and posterior gastric walls 18, 20 for the creation of a patterned suture stitch 22, for example, a mattress stitch pattern, within the stomach 24, preferably a mattress stitch suture pattern. The patterned suture stitch 22 is positioned to extend from the proximal end 26 to the distal end 28 of the stomach 24 in a manner creating a reduced passageway when the suture 22 is pulled upon to cause the anterior and posterior walls 18, 20 of the stomach 24 to come together. While a mattress stitch pattern is disclosed in accordance with a preferred embodiment of the present invention, those skilled in the art will appreciate that other suture stitch patterns may be used without departing from the spirit of the present invention.

Although the present apparatus is described herein for use in performing gastric reduction surgery, those skilled in the art will appreciate the apparatus and the underlying concepts may be applied in various soft tissue apposition procedures where tissue is drawn together either permanently or temporarily.

The longitudinally extending applier 30 of the present gastric reduction apparatus 10 includes a distal end 32 and a proximal end 34. The shaft 14 and a handle 38 are secured to the applier 30 for actuation thereof in a manner discussed below in greater detail.

The applier 30 generally includes a longitudinally extending applier body 40 having a posterior suction slot 42 and an anterior suction slot 44. The posterior and anterior suction slots 42, 44 are shaped and dimensioned for receiving tissue therein. The slots 42, 44 extend along the longitudinal axis of the applier body 40 defining recesses into which the posterior and anterior stomach tissue at the stomach walls 18, 20 may be drawn during the application of pledgets 16 as discussed below.

The proximal end 34 of the applier 30 includes a barbed attachment member 46 shaped and dimensioned for attachment to the support shaft 14 of the instrument. The barbed attachment member 46 brings the applier body 40 into communication with the suction line 48 of the support shaft 14 for the creation of a vacuum within the posterior and anterior suction slots 42, 44.

As discussed above, the posterior and anterior suction slots 42, 44 are shaped and dimensioned for allowing stomach tissue at the stomach walls 18, 20 to be suctioned therein such that the tissue comes into intimate contact with three sides of a series of pledgets 16 previously mounted along the applier body 40. Although the suction slots 42, 44 and pledgets 16 provide for tissue contact along three sides in accordance with a preferred embodiment, those skilled in the art will appreciate the specific shape may be varied and the tissue need only come into intimate contact with the interior surface of the pledgets 16.

The pledgets 16 are mounted along the length of the applier body 40 for selective coupling with tissue suctioned within the posterior and anterior suction slots 42, 44 in a manner discussed below in greater detail. The pledgets 16 are respectively mounted within transverse pledget recesses 50 formed within the applier body 40. A first series of pledget recesses 50 are formed along the anterior suction slot 44 for the application of pledgets 16 to the anterior stomach wall 18 and a second series of pledget recesses 50 are formed along the posterior suction slot 42 for the application of pledgets 16 to the posterior stomach wall 20. Prior to use, open pledgets 16 are seated within the respective pledget recesses 50 for subsequent application within the stomach walls 18, 20.

In accordance with a preferred embodiment of the present invention, each of the pledgets 16 is composed of a two-part construction generally including a pledget body 52 and a needle 54. The two-part construction offers very low firing force resulting from the limited yield of the materials employed in accordance with the present invention. In addition, and as is discussed below in greater detail, the pledget body 52 and the needle 54 are shaped and dimensioned to permit piercing of full tissue thickness during actuation and receive a suture for facilitating the prewoven suture configuration employed in accordance with present invention. The pledgets 16 also provide for locking of the needle 54 after actuation thereof.

More particularly, each of the pledgets 16 includes a U-shaped pledget body 52 defining an opening 53 over which the needle 54 moves to close the opening 53 and secure tissue therein. Opposite the pledget opening 53 is a pledget aperture 56 through which a suture 22 is passed prior to placement of the pledget 16 within a pledget recess 50.

The pledget body 52 includes first and second upwardly extending arms 80,82 connected by a central connecting member 84. The free end 68 of the second upwardly extending arm 82 includes a dovetail shaped slot 90 shaped and dimensioned for securely retaining and guiding the needle 54 as it is moved across the opening 53 toward the free end 86 of the first upwardly extending arm 80 of the pledget body 52. The free end 86 of the first upwardly extending arm 80 similarly includes a dovetail shaped slot 88 shaped and dimensioned for receiving the front end of the needle 54 as it is moved across the opening during actuation.

Each of the needles 54 is also provided with an abutment surface 92 to prevent further movement when the needle fully extends across the opening 53. A spring clip 70 is also provided adjacent the end of each of the needles 54 for preventing rearward movement of the needles 54 after firing thereof. The spring clip 70 is generally a gripping member shaped and dimensioned to grab the upper surface 94 of the second upwardly extending arm 82 after the needle 54 has been moved across the opening 53. The spring clip 70 includes a forward facing, lower ramp 96 shaped and dimensioned to slide over the forward facing portion 98 of the upper surface 94 of the second upwardly extending arm 82 as the needle 54 moves toward its locked position.

Movement of the spring clip 70 over the forward facing portion 98 of the second upwardly extending arm 82 causes a slight bias in the cut out 100 of the second upwardly extending arm 82 and the rearward facing locking surface 102 of the spring clip "snaps" into engagement with the rearward facing upper surface 104 of the second upwardly extending arm 82 once the lower ramp 96 passes the forward facing portion 98 during movement of the needle 54. Upon firing and movement of the needles 54, respective spring clips 70 prevent backup of the needles 54. The clips 70 thereby lock the needles 54 in their rotated position.

In accordance with a preferred embodiment of the present invention, the pledgets 16 are prestrung with a suture 22 passing through the apertures 56. As such, and as discussed below in greater detail, the pledgets 16 are preferably secured to the tissue at the stomach walls 18, 20 with a suture 22 attached thereto via the pledget aperture 56 for simple implementation of the present method.

Actuation of the pledgets 16 is achieved via a firing mechanism 58. The firing mechanism 58 includes the previously mentioned handle 38 which links the proximal end of the shaft 14 with the applier 30 located at the distal end 12 of the support shaft 14. The handle 38 allows for the controlled actuation of firing wedges 106, 108 that cause the needles 54 of the pledgets 16 to rotate across the respective posterior and anterior suction slots 42, 44, securing the pledgets 16 to the stomach tissue.

In accordance with a preferred embodiment of the present invention, a pair of firing wedges 106, 108 are used in actuation of the respective pledgets 16 for movement of the needles 54 across the openings 53 of the respective pledgets 16. Briefly, the firing wedges 106, 108 are advanced along the length of the applier body 40 to sequentially engage and move the needles 54 of the pledgets 16 positioned along the length of the applier body 40. The first firing wedge 106 fires the needles 54 along the posterior suction slot 42 and the second firing wedge 108 fires the needles 54 along the anterior suction slot 44.

The firing wedges 106, 108 are substantially identical. The first firing wedge 106 is described herein and those skilled in the art will certainly, therefore, appreciate the construction and operation of the second firing wedge 108. The first firing wedge 106 includes a main body 110 with a forward facing surface 112 shaped and dimensioned for engaging a cam surface 114 along the rear end of the needles 54. The forward facing surface 112 is tapered and engages the cam surface 114 of the needles 54 in a manner which forces the needles 54 in a direction substantially perpendicular to the direction in which the first firing wedge 106 is traveling during actuation of the present apparatus. Although the present embodiment employs a straight edge along the forward facing surface of the firing wedge, those skilled in the art will appreciate that the forward facing surface of the first firing wedge may be formed with a variety of profiles capable of causing lateral needle movement without departing from the spirit of the present invention.

The first firing wedge 106 is supported for movement along the length of the applier body 40 by a dovetail shaped track 116 formed in the wall of the applier body 40. With this in mind, the first firing wedge 106 is provided with a coupling member 117 shaped and dimensioned to fit within the track 116 for movement relative thereto. In accordance with a preferred embodiment, the track 116 is a dovetail shaped recess and the coupling member is a dovetail shaped joint shaped and dimensioned to securely fit within the recess of the track 116.

In practice, the first firing wedge 106 is drawn along the applier body 40 under the control of the firing cable 118, which is actuated from the handle 38 of the present apparatus. As the firing cable 118 draws the firing wedge 106 along the track 116, the angled forward facing surface 112 of the first firing wedge 106 contacts the cam surfaces 114 of each respective needle 54, which also ride in their own dovetail slots 90. The needle 54 is cammed about the longitudinal axis of the applier body 40, piercing tissue and finally mating with the first upwardly extending arm 80 of the pledget body 52. At this point, the spring clip 70 engages with the second upwardly extending arm 82 of the pledget body 52, fully constraining the needle in its actuated position.

Once fully fired, the needles 54 span the openings of the pledgets 16 and the tissue trapped therein serves as the anchor material for the pledgets 16. The needles 54 run into walls in the receiving recesses 90 of the respective pledgets 16. The walls engage the abutment member 92 and limit forward motion of the needles from the second upwardly extending arm 82 to the first upwardly extending arm 80.

As discussed above, a spring clip 70 prevents rearward movement of the needles 54 after firing thereof. The spring clip 70 grabs the rearward facing upper surface 104 of the second upwardly extending arm 82 after the needle 54 has been moved across the opening 53. Upon firing and movement of the needles 54, respective spring clips 70 prevent backup of the respective needles 54. The clips 70 thereby lock the needles 54 in their rotated position.

A pre-threaded suture 22 goes through the suture apertures 56 formed in the pledgets 16. As a result, the suture 22 is attached to the tissue by means of the pledgets 16 and needles 54. This provides for the ability to fire the pledgets 16 and then join them in a second step.

Once firing is accomplished, the suction applied to the applier 30 is removed and replaced with insufflation. This pushes the stomach walls apart which in turn pulls the attached pledgets 16 out of their transverse pledget recesses 50 within the applier body 40 and the applier body 40 may thereafter be extracted from the stomach cavity.

What remains is a series of pledgets 16 secured along the anterior and posterior walls 18, 20 of the stomach 24 with pre-threaded sutures 22 extending from pledget 16 to pledget 16 in a manner defining an uncinched mattress stitch or other stitch pattern. The distal end 72 of the uncinched mattress stitch suture 22 is fastened securely to the distal most pledget 16 and the proximal end 74 of the uncinched mattress stitch suture 22 is visible to the surgeon via the gastroscope 14.

Once the suture 22 is extracted from the applier body 40, and the uncinched mattress stitch suture 22 remains within the stomach 24, the suture 22 is simply cinched down by drawing upon the proximal end 74 of the pre-threaded suture 22. This causes the stomach walls 18, 20 to be drawn together creating a desired gastric restriction. While suture line cinching is disclosed above in accordance with a preferred embodiment, tissue cinching may be accomplished in a variety of manners without departing from the spirit of the present invention.

Figure 2:
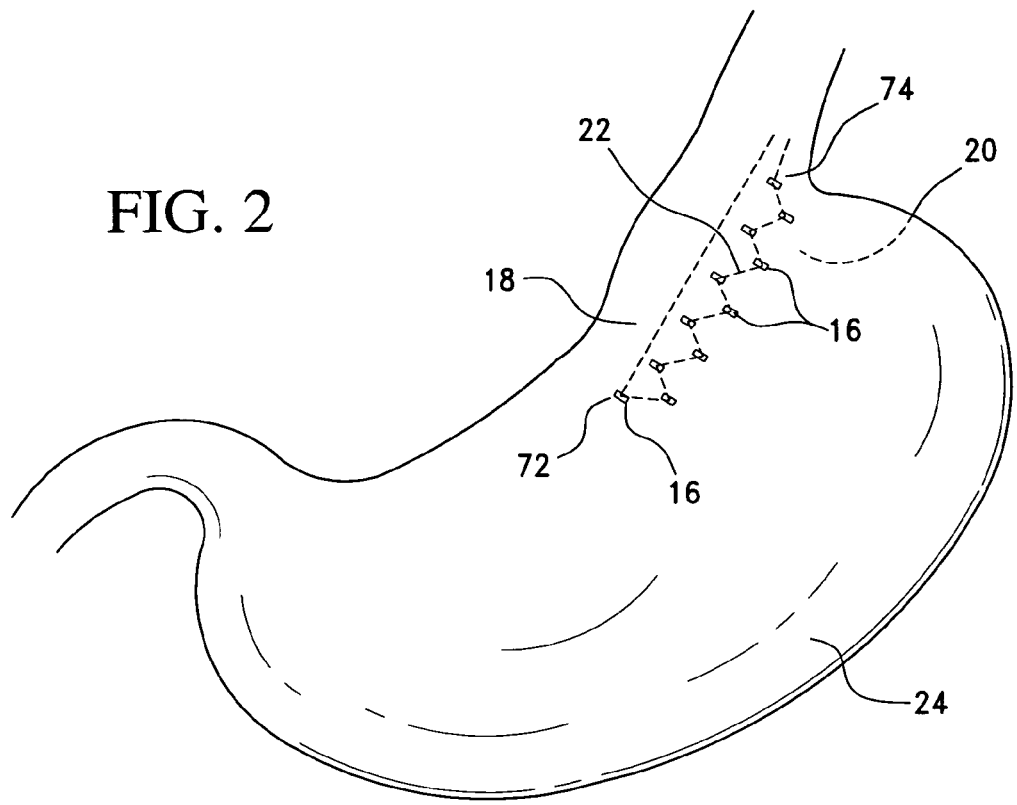
FIG. 2 is a view of uncinched pledgets deployed within the stomach.
Figure 3:
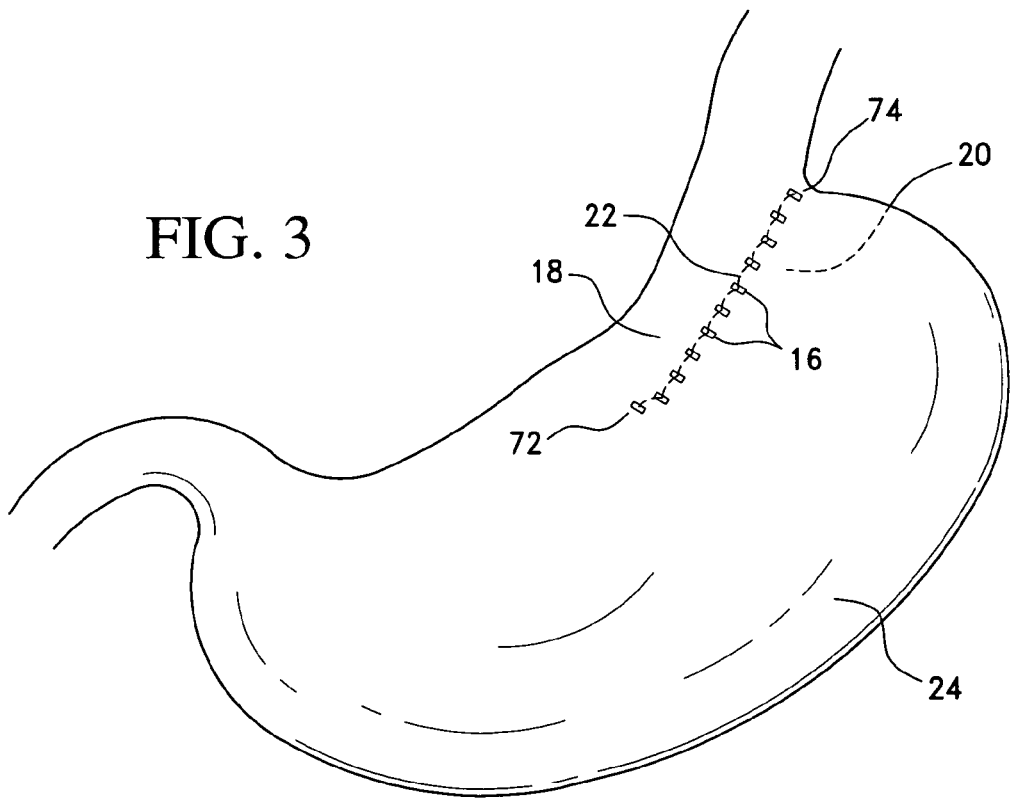
FIG. 3 is a view of cinched pledgets deployed within the stomach.
Figure 9:
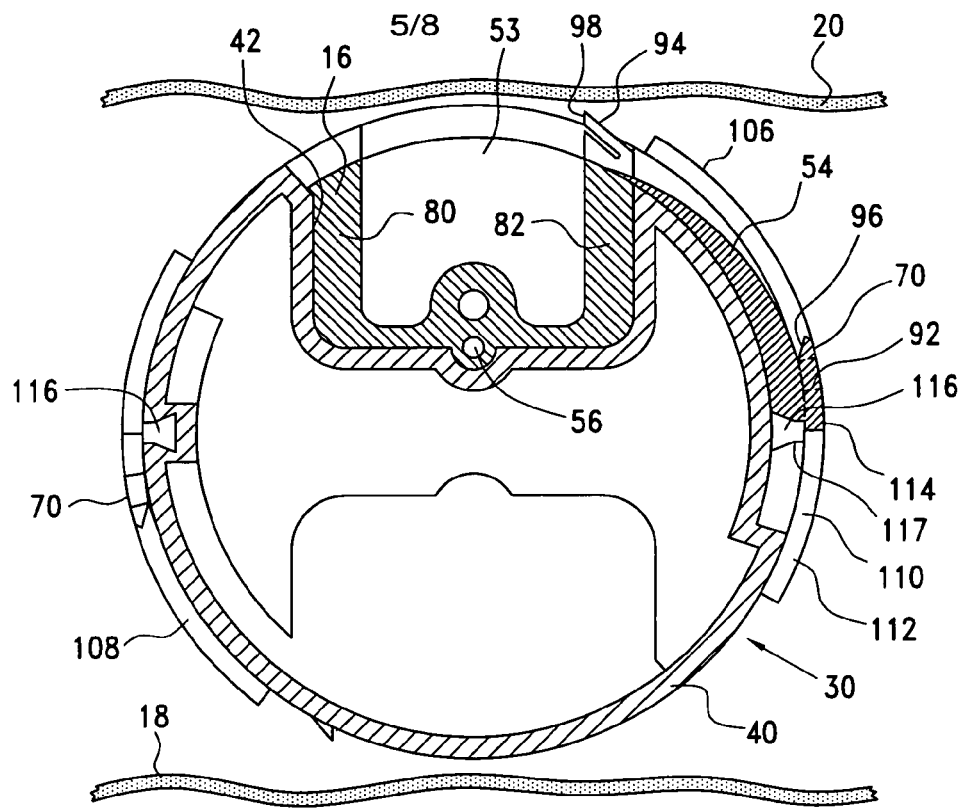
FIGS. 9 and 10 are cross sectional views showing application of a pledget in accordance with the present invention.
Figure 10:
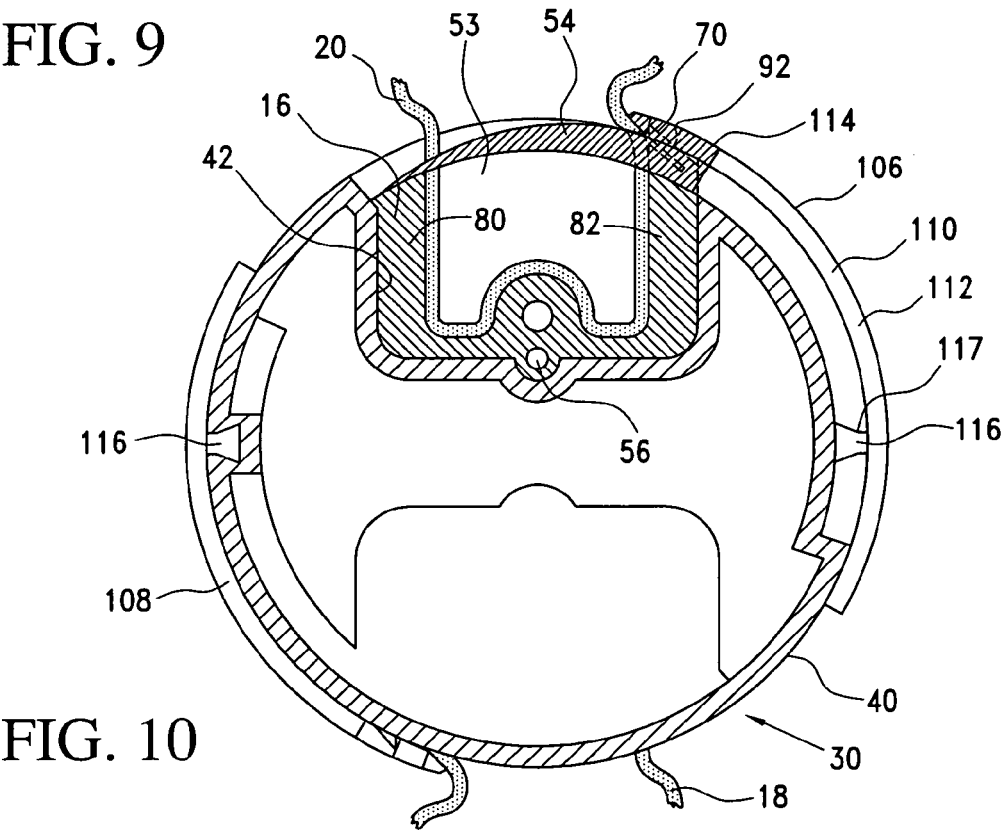
Figure 12:
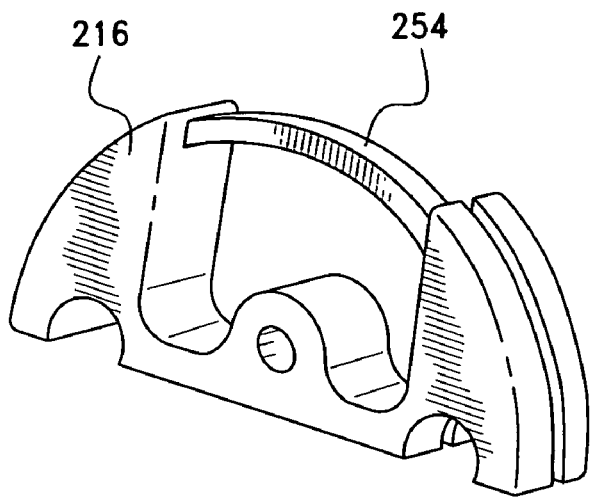
FIG. 12 is a perspective view of a pledget employed with the embodiment disclosed in FIGS. 13 through 16.
Figure 11:
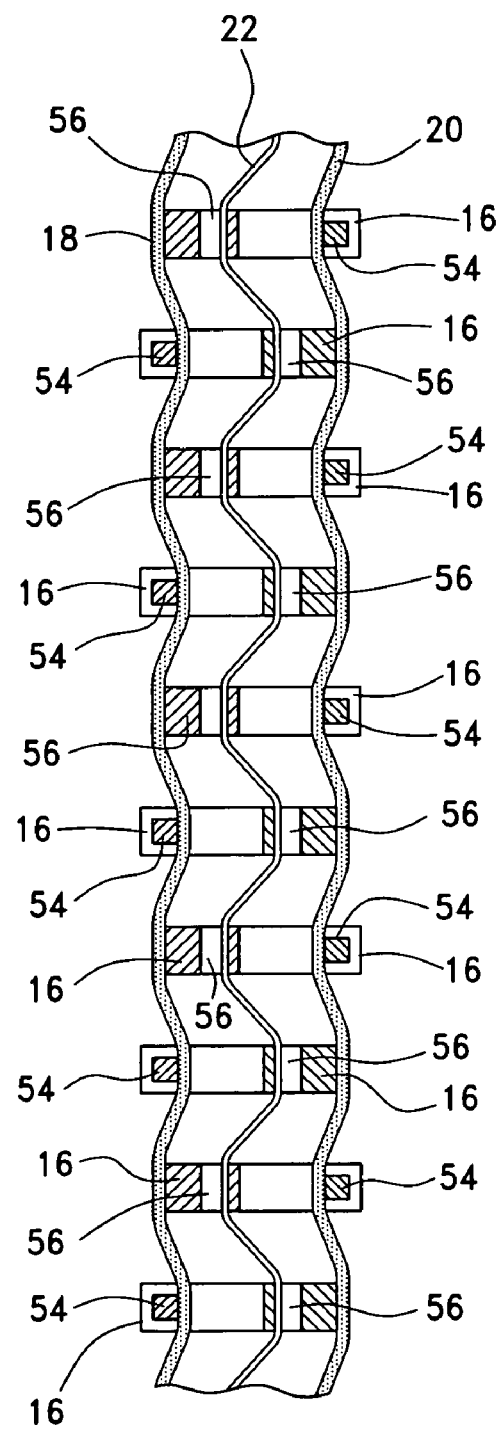
FIG. 11 is a cross sectional view of the pledgets secured to appose stomach tissue with a pre-strung suture.
Figure 13:
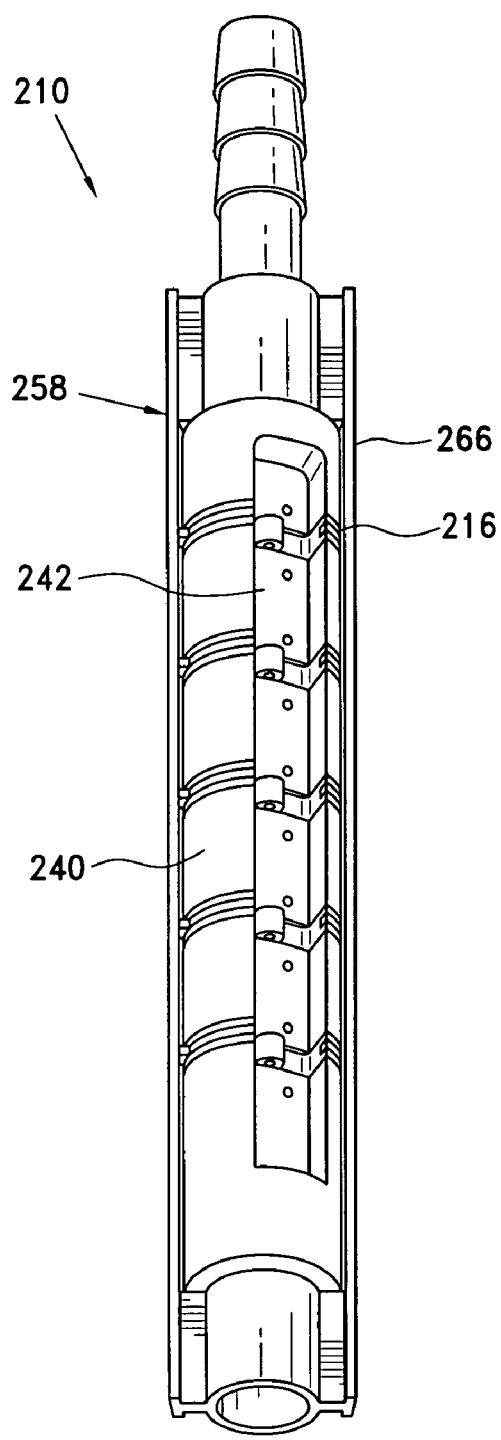
FIGS. 13 and 14 are perspective views of the anterior and posterior sides of an alternate embodiment of the present invention.
Figure 14:
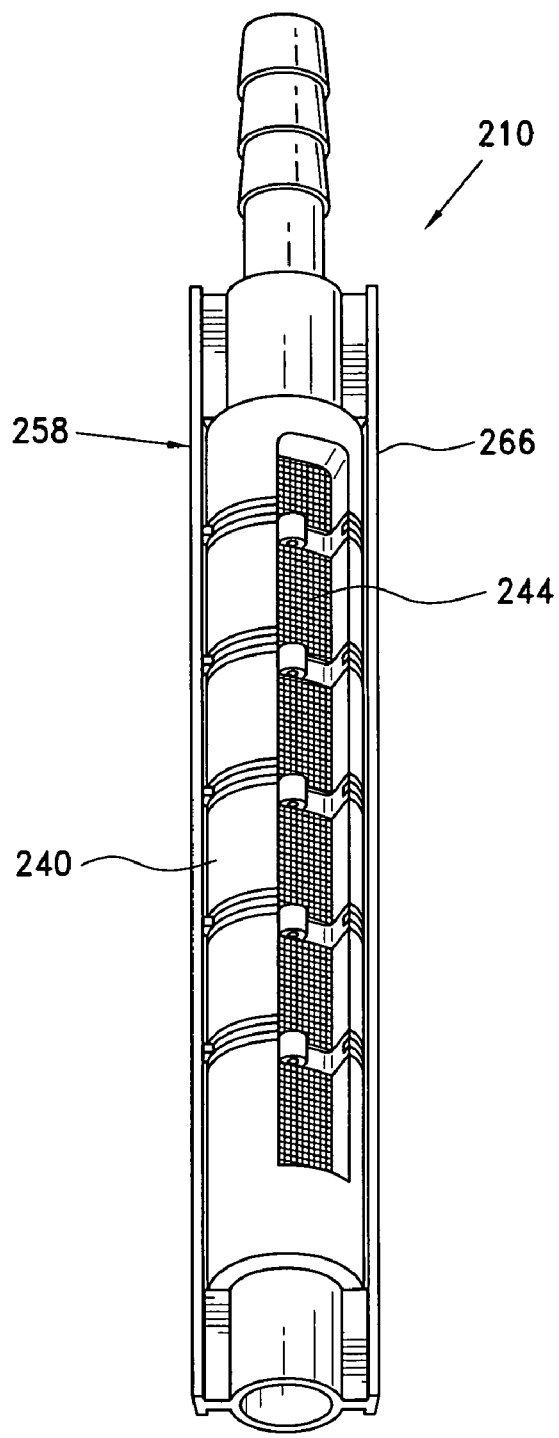
Figure 15:
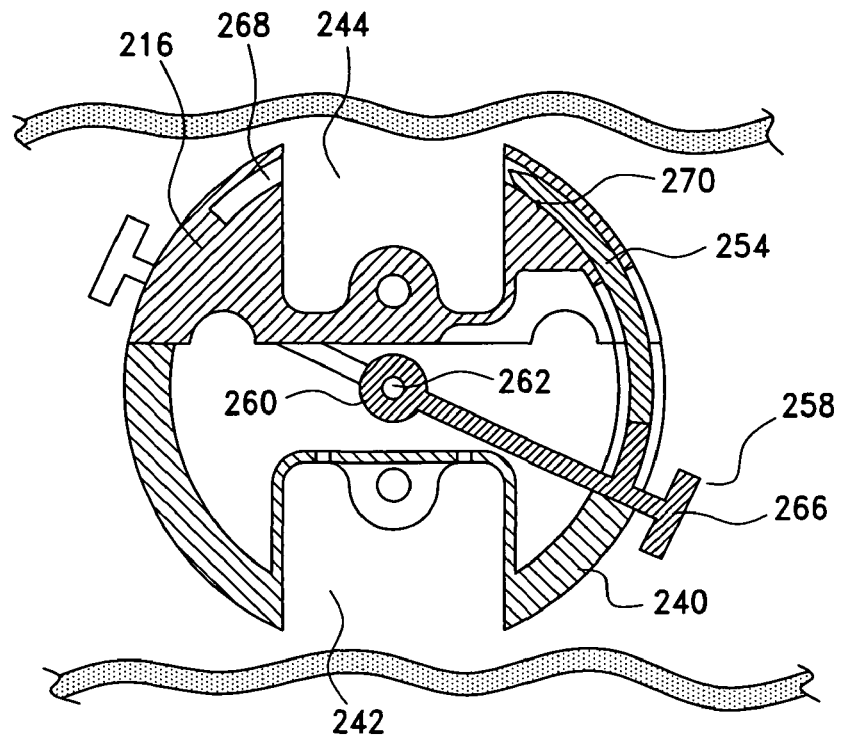
FIGS. 15 and 16 are cross sectional views showing application of a pledget in accordance with the embodiment disclosed with reference to FIGS. 13 and 14.
Figure 16:
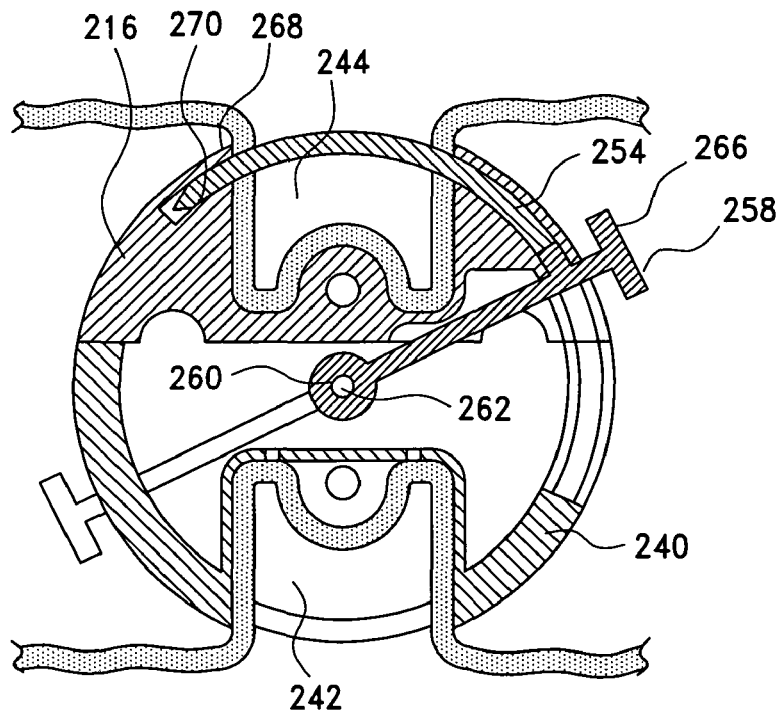

Referring to FIG. 2, the resulting structure of the stomach is that of a tubular member. The tubular member may extend the full length between the esophagus and the pylorus or extend only a portion of the distance from the esophagus to the pylorus. Regardless of the length of the tubular member, the gastric remnant allows gastric acid to pass into the food stream. This produces a smaller stomach volume as well as a restrictive means for the bolus.

While suture line cinching is disclosed above in accordance with a preferred embodiment, tissue cinching may be accomplished by throwing a sliding knot, tied outside the body, down the mouth and esophagus. Alternatively, a suture clip, such as those sold by Ethicon Endo-Surgery, Inc., may be placed over the cinched suture at the point of the proximal most thread.

In accordance with an alternate embodiment, and with reference to FIGS. 12 to 16, actuation of the needles 254 may be achieved via a firing bar 266 and firing hub 260 actuated from the proximal end of the apparatus 210. In general, the firing mechanism 258 relies upon the controlled actuation of firing hubs 260 that cause the needles 254 of the pledgets 216 to be rotated across the respective posterior and anterior suction slots 242, 244, securing the pledgets 216 to the stomach tissue. In use, and after the tissue is sucked within the anterior and posterior suction slots 242, 244, the firing hubs 260 of the firing mechanism 258 are actuated via a firing rod 262 solidly connected to the firing hubs 260. Rotation of the firing rod 262 causes the firing hubs 260 to rotate correspondingly. This causes the firing bar 266 to rotate about the center of the applier body 240. The firing bar 266 in turn pushes the needles 254 of the pledgets 216 across the pledgets 216 such that the needles 254 pierce stomach tissue. Operation is further enhanced by providing a firing bar 266 that fires all the needles 154 of the various pledgets 116 simultaneously.

Once fully fired, the needles 254 span the openings of the pledgets 216 and the tissue trapped therein serves as the anchor material for the pledgets 216. The needles 254 run into walls of the receiving slots 268 of the respective pledgets 216 to limit forward motion of the needles 254. A spring clip 270 is provided adjacent the end of each of the needles 254 for preventing rearward movement of the needles 254 after firing thereof. More specifically, the spring clip 270 is a biased stop arm depressed by the needles 254 when they are in their prefired orientation. Upon firing and movement of the needles 254, respective spring clips 270, which were previously depressed by the needles 254, spring up and prevent backup of the needles 254, thus locking the needles 254 in their rotated position.

In accordance with further alternate embodiments, it is contemplated that a suction mesh may be utilized. The suction mesh, which is comprised of layers of screen mesh disposed in layers at angles, prevents suctioned tissue from plugging the suction holes and allow for the distribution of suction. The suction mesh also enhances the surface area over which the tissue is controlled. The suction mesh could be placed at the base of a suction slot and on the slot sidewalls for increasing suction.

In addition, a stainless steel or polymeric Velcro, which would have the same effect as the suction mesh, could be placed over the base of the suction slot. After release of the pledgets, the Velcro would help attached the posterior and anterior walls of the stomach more permanently, thus resisting some of the wear on the sutures inherent in the stomach motions. The hooks on the one side and claws on the others would be trapped between the pledgets and the tissue for sure retention on the stomach wall.

Once the suture is fully positioned, inspection may be achieved using a distally mounted camera that plugs into the endoscopic device to ensure that the gastric wall has been folded in a proper orientation. The camera may be mounted on an articulating or retro-flexing arm to visualize backward on the instrument. Alternatively, a two camera unit may be utilized. The two camera unit would be designed to show both forward and rearward views. Additionally, an optical fiber bundle may be placed down the center of the apparatus. Further, the proximal end of the fiber can then be coupled to an endoscope to provide a rudimentary image sufficient for guiding the scope down. Although a preferred embodiment is disclosed above, various alternatives have been developed. For example, tubes may be placed over the sutures. The tubes between the pledgets would act as spacers so that the sutures do not draw the tissue closer longitudinally. This would preserve the pouch length during cinching. In addition, the spacer tubes could be placed between the initial and final fasteners to act as a single length preserving spacer.

As those skilled in the art will certainly appreciate, the present apparatus may be combined with other surgical procedures and apparatuses to provide for more permanent fixation. For example, this energy based tissue injury mechanism would serve to intentionally cause damage to tissue to promote healing after the tissue is apposed. The incorporation of the tissue damage on the device in parallel with existing fastening technology ensures repeatable positioning of the fasteners relative to the injured portion of tissue. The injury mechanism as currently conceived is comprised of two bipolar or monopolar strips each disposed at the bottom surface of the suction slots, and which, on activation, damage tissue. In addition, various tissue glues may be employed to enhance seals created in accordance with the present invention Fibrin based tissue glues available on the market can be disposed on the bottom surfaces of the suction slots so as to contact the tissue being suctioned into said slots. This glue reduces loading on the fasteners apposing tissue, increasing effective holding duration.

As those skilled in the art will certainly appreciate, the invention differs from the devices existing in the prior art in that it is used, not as a repair suture technique, but is rather used as a mechanism for approximating two walls not normally in contact with tissue. Further, the cinching media is not an elastomer, but rather it is a polymer. The anchor or pledget gains positive tissue control by entering and exiting tissue such that in the absence of traction, the pledget will remain engaged. The suture is unreleasably engaged with the anchor of the pledget. As a result, it cannot, in the absence of tension, let go of the anchors.

While the preferred embodiments have been shown and described, it will be understood that there is no intent to limit the invention by such disclosure, but rather, is intended to cover all modifications and alternate constructions failing within the spirit and scope of the invention.

The invention claimed is:

1. An endoscopic gastric reduction apparatus adapted for applying a series of pledgets to anterior and posterior gastric walls for the creation of a patterned suture stitch within the stomach, comprising:
   an applier having a distal end and a proximal end, the applier being secured at a distal end of a support shaped and dimensioned for passage down the esophagus and into the stomach;
   the applier includes an applier body having a posterior suction slot and an anterior suction slot;
   a plurality of pledgets housed within the respective anterior suction slot and the posterior suction slot;
   the anterior and posterior suction slots being shaped and dimensioned for receiving tissue therein for application of the plurality of pledgets housed within the respective anterior suction slot and the posterior suction slot, the plurality of pledgets being prestrung with a suture housed within the applier body and extending between pledgets respectively housed within the anterior suction slot and the posterior suction slot for selective coupling with tissue suctioned within the posterior suction slot and the anterior suction slot.

2. The gastric reduction apparatus according to claim 1, wherein the posterior suction slot and the anterior suction slot extend along a longitudinal axis of the applier body defining recesses into which posterior and anterior stomach tissue may be drawn during the application of pledgets.

3. The gastric reduction apparatus according to claim 2, wherein the plurality of pledgets are mounted within the anterior and posterior suction slots, the plurality of pledgets being mounted along the length of the applier body for selective coupling with tissue suctioned within the posterior suction slot and the anterior suction slot.

4. The gastric reduction apparatus according to claim 3, wherein the plurality of pledgets are respectively mounted within transverse pledget mounting locations formed within the applier body.

5. The gastric reduction apparatus according to claim 4, wherein a first series of pledget recesses are formed along the anterior suction slot for application of the plurality of pledgets to the anterior stomach wall and a second series of pledget recesses are formed along the posterior suction slot for application of the plurality of pledgets to the posterior stomach wall.

6. The gastric reduction apparatus according to claim 1, further including a firing mechanism that actuates the plurality of pledgets for fastening to tissue.

7. The gastric reduction apparatus according to claim 6, wherein the firing mechanism includes a firing wedge actuating the plurality of pledgets for selective closing thereof.

8. The gastric reduction apparatus according to claim 1, wherein a proximal end of the applier body includes a barbed attachment member shaped and dimensioned for attachment to the support.

9. The gastric reduction apparatus according to claim 8, wherein the barbed attachment member brings the applier body into communication with a suction line of the support for the creation of a vacuum within the anterior suction slot and the posterior suction slot.

10. The gastric reduction apparatus according to claim 1, wherein the plurality of pledgets are mounted along the length of the applier body for selective coupling with tissue suctioned within the anterior suction slot and the posterior suction slot.

11. The gastric reduction apparatus according to claim 10, wherein the plurality of pledgets are respectively mounted within transverse pledget recesses formed within the applier body.

12. A pledget for fastening to tissue, comprising:
a pledget body supporting a needle for movement relative thereto, the pledget body defining a pledget opening over which the needle moves to close the pledget opening and secure tissue therein;
the pledget body further including first and second upwardly extending arms connected by a central connecting member, the central connecting member including an aperture shaped and dimensioned for the passage of a suture prior to use of the pledget, the second upwardly extending arm including a slot shaped and dimensioned for securely retaining and guiding the needle as it is moved from the second arm toward the first arm, and wherein the movement of the needle is relative to the first upwardly extending arm and the second upwardly extending arm across the pledget opening.

13. The pledget according to claim 12, wherein the needle moves between an open position and a closed position spanning the pledget opening with tissue trapped therein serving as the anchor material for the pledget.

14. The pledget according to claim 13, wherein the pledget body includes a receiving recess that limits forward motion as the needle moves between the open position and the closed position.

15. The pledget according to claim 13, wherein the needle includes a means for preventing rearward movement of the needle after firing thereof.

16. The pledget according to claim 12, wherein the first upwardly extending arm includes a slot shaped and dimensioned for receiving a front end of the needle as it is moved toward the first upwardly extending arm.

17. The pledget according to claim 12, where the needle is provided with a spring clip preventing rearward movement of the needle relative to the pledget body.

18. The pledget according to claim 17, wherein the spring clip is shaped and dimensioned to grab a surface of the second upwardly extending arm after the needle has been moved across the opening.

19. An endoscopic gastric reduction apparatus adapted for applying a series of pledgets to anterior and posterior gastric walls for the creation of a patterned suture stitch within the stomach, comprising:
an applier having a distal end and a proximal end, the applier being secured at a distal end of a support shaft shaped and dimensioned for passage down the esophagus and into the stomach;
the applier includes an applier body having a posterior suction slot and an anterior suction slot, the anterior and posterior suction slots being shaped and dimensioned for receiving tissue therein; and
a series of pledgets housed within the respective anterior suction slot and posterior suction slot, the series of the pledgets being prestrung with a suture mounted within the applier body and extending between the pledgets respectively housed with the anterior suction slot and the posterior suction slot, the pledgets and suture being mounted along the length of the applier body for selective coupling with tissue suctioned within the anterior suction slot and the posterior suction slot.

20. The gastric reduction apparatus according to claim 19, wherein a first series of pledget recesses are formed along the anterior suction slot for application of the pledgets to the anterior stomach wall and a second series of pledget recesses are formed along the posterior suction slot for application of the pledgets to the posterior stomach wall.

21. The gastric reduction apparatus according to claim 19, further including a firing mechanism that actuates the pledgets for fastening to tissue.

22. An endoscopic gastric reduction apparatus adapted for applying a series of pledgets to anterior and posterior gastric walls for the creation of a patterned suture stitch within the stomach, comprising:
an applier having a distal end and a proximal end, the applier being secured at a distal end of a support shaped and dimensioned for passage down the esophagus and into the stomach;
the applier includes an applier body having a posterior suction slot extending along a longitudinal axis of the applier body and including a first series of pledget recesses in which a first plurality of pledgets are housed and an anterior suction slot extending along the longitudinal axis of the applier body and including a second series of pledget recesses in which a second plurality of second pledgets are housed, the anterior and posterior suction slots facing opposed anterior and posterior gastric walls and being shaped and dimensioned for receiving tissue therein for application of a plurality of pledgets housed within the respective anterior suction slot and the posterior suction slot, the plurality of pledgets being prestrung with a suture housed within the applier body and extending between pledgets respectively housed within the anterior suction slot and the posterior suction slot for selective coupling with tissue suctioned within the posterior suction slot and the anterior suction slot.

23. The gastric reduction apparatus according to claim 22, further including a firing mechanism that actuates the first and second pluralities of pledgets for fastening to tissue.

24. The gastric reduction apparatus according to claim 23, wherein the firing mechanism includes a firing wedge actuating the first and second pluralities of pledgets for selective closing thereof.

25. The gastric reduction apparatus according to claim 22, wherein a proximal end of the applier body includes a barbed attachment member shaped and dimensioned for attachment to the support.

26. The gastric reduction apparatus according to claim 25, wherein the barbed attachment member brings the applier body into communication with a suction line of the support for the creation of a vacuum within both the anterior suction slot and the posterior suction slot.

27. The gastric reduction apparatus according to claim 22, wherein the first and second pluralities of pledgets are mounted along the length of the applier body for selective coupling with tissue suctioned within the suction slot.

28. An endoscopic gastric reduction apparatus adapted for applying a series of pledgets to anterior and posterior gastric walls for the creation of a patterned suture stitch within the stomach, comprising:
- an applier having a distal end and a proximal end, the applier being secured at a distal end of a support shaft shaped and dimensioned for passage down the esophagus and into the stomach;
- the applier includes an applier body having a posterior suction slot and an anterior suction slot, the anterior and posterior suction slots being shaped and dimensioned for receiving tissue therein; and
- a series of pledgets housed within the respective anterior suction slot and posterior suction slot, the series of the pledgets being prestrung with a suture mounted within the applier body and extending between the pledgets respectively housed with the anterior suction slot and the posterior suction slot, the pledgets and suture being mounted along the length of the applier body for selective coupling with tissue suctioned within the anterior suction slot and the posterior suction slot; and
- each pledget including a pledget body supporting a needle for movement relative thereto, the pledget body defining a pledget opening over which the needle moves to close the pledget opening and secure tissue therein, the pledget body further including first and second upwardly extending arms connected by a central connecting member, the central connecting member including an aperture shaped and dimensioned for the passage of a suture prior to use of the pledget, the second upwardly extending arm including a slot shaped and dimensioned for securely retaining and guiding the needle as it is moved from the second arm toward the first arm, and relative to the first upwardly extending arm and the second upwardly extending arm across the pledget opening.

29. The gastric reduction apparatus according to claim 28, wherein a first series of pledget recesses are formed along the anterior suction slot for application of the pledgets to the anterior stomach wall and a second series of pledget recesses are formed along the posterior suction slot for application of the pledgets to the posterior stomach wall.

30. The gastric reduction apparatus according to claim 28, further including a firing mechanism that actuates the pledgets for fastening to tissue.

* * * * *